United States Patent [19]
Dean et al.

[11] Patent Number: 5,997,844
[45] Date of Patent: *Dec. 7, 1999

[54] TECHNETIUM-99M LABELED PEPTIDES FOR IMAGING

[75] Inventors: Richard T. Dean, Bedford; Scott Buttram, Derry; William McBride, Manchester; John Lister-James, Bedford; Edgar R. Civitello, Bradford, all of N.H.

[73] Assignee: Diatide, Inc., Londonderry, N.H.

[ * ] Notice: This patent is subject to a terminal disclaimer.

[21] Appl. No.: 08/253,678

[22] Filed: Jun. 3, 1994

Related U.S. Application Data

[63] Continuation-in-part of application No. 07/653,012, Feb. 8, 1991, abandoned, and application No. 08/092,355, Jul. 15, 1993.

[51] Int. Cl.⁶ .......................... A61K 51/00; A61M 36/14
[52] U.S. Cl. .................. 424/1.69; 424/1.11; 424/1.65; 424/9.1; 534/10; 534/14; 530/300; 530/331; 530/329; 530/326; 530/327; 530/328; 530/330
[58] Field of Search ................................ 424/1.67, 1.69, 424/1.11, 9.1; 206/569, 223, 570; 534/14, 7, 10–16; 530/300, 324, 325, 326, 327, 328, 329, 330, 331

[56] References Cited

U.S. PATENT DOCUMENTS

| | | |
|---|---|---|
| 4,434,151 | 2/1984 | Byrne et al. . |
| 4,444,690 | 4/1984 | Fritzberg . |
| 4,472,509 | 9/1984 | Gansow et al. . |
| 4,571,430 | 2/1986 | Byrne et al. .......................... 424/1.11 |
| 4,575,556 | 3/1986 | Byrne et al. . |
| 4,615,876 | 10/1986 | Troutner et al. . |
| 4,673,562 | 6/1987 | Eg et al. . |
| 4,832,940 | 5/1989 | Ege . |
| 4,861,869 | 8/1989 | Nicolotti et al. . |
| 4,965,392 | 10/1990 | Fritzberg et al. . |
| 4,986,979 | 1/1991 | Morgan, Jr. et al. .................. 424/1.11 |
| 4,988,496 | 1/1991 | Srinivasan et al. ..................... 424/1.11 |
| 5,061,641 | 10/1991 | Shochat et al. . |
| 5,225,180 | 7/1993 | Dean et al. ............................ 424/1.11 |
| 5,279,811 | 1/1994 | Bergstein et al. . |
| 5,382,654 | 1/1995 | Lyle et al. ................................. 534/10 |
| 5,405,597 | 4/1995 | Dean et al. ............................. 424/1.69 |
| 5,443,815 | 8/1995 | Dean et al. ............................. 424/1.69 |
| 5,552,525 | 9/1996 | Dean ..................................... 530/326 |
| 5,654,272 | 8/1997 | Dean ......................................... 514/12 |
| 5,686,410 | 11/1997 | Albert et al. ............................... 514/12 |
| 5,811,394 | 9/1998 | Dean ......................................... 514/12 |

FOREIGN PATENT DOCUMENTS

| | | |
|---|---|---|
| 82301700 | 10/1982 | European Pat. Off. . |
| 85104959 | 12/1985 | European Pat. Off. . |
| 174853 | 3/1986 | European Pat. Off. . |
| 188256 | 6/1986 | European Pat. Off. . |
| 86100360 | 7/1986 | European Pat. Off. . |
| 86105920 | 11/1986 | European Pat. Off. . |
| 88102252 | 8/1988 | European Pat. Off. . |
| 398143 | 11/1990 | European Pat. Off. . |
| 0 403 243 A1 | 12/1990 | European Pat. Off. . |
| 403243 | 12/1990 | European Pat. Off. . |
| 90306428 | 12/1990 | European Pat. Off. . |
| 90402206 | 2/1991 | European Pat. Off. . |
| WO9101144 | 2/1991 | European Pat. Off. . |
| WO88900051 | 1/1989 | WIPO . |
| WO8902752 | 4/1989 | WIPO . |
| WO8912680 | 6/1989 | WIPO . |
| WO8907456 | 8/1989 | WIPO . |
| WO8910759 | 11/1989 | WIPO . |
| WO8910760 | 11/1989 | WIPO . |
| WO8912625 | 12/1989 | WIPO . |
| WO8912680 | 12/1989 | WIPO . |
| WO9010463 | 9/1990 | WIPO . |

(List continued on next page.)

OTHER PUBLICATIONS

Tubis et al., 1968, "The Preparation of $^{99m}$Technetium–Labeled Cystine, Methionine and a Synthetic Polypeptide and their Distribution in Mice", *Int. J. Appl. Rad. Isot.* 19: 835–840.

Sundrehagen, 1983, "Formation of a [$^{99m}$Tc]Polypeptide Hormone: Characterization and Chemical Quality Control by Ampholyte Displacement Radiochromatography", *Int. J. Appl. Rad. Isot.* 34: 1003.

Bryson et al., 1988, "Neutral Technetium(V) Complexes with Amide–Thiol–Thioether Chelating Ligands", *Inorg. Chem.* 27: 2154–2161.

Misra et al., 1989, "Synthesis of a Novel Diaminodithiol Ligand for Labeling Proteins and Small Molecules with Technetium–99m", *Tet. Lett.* 30: 1885–1888.

Baidoo & Lever, 1990, "Synthesis of a Diaminedithiol Bifunctional Chelating Agent for Incorporation of Technetium–99m into Biomolecules", *Bioconjugate Chem.* 1: 132–137.

Bryson et al., 1990, "Protecting Groups in the Preparation of Thiolate Complexes of Technetium", *Inorg. Chem.* 29: 2948–2951.

Taylor et al., 1990, "Brain Uptake and Retention of [Tc–99m]T691: A Potential New Tracer of Cerebral Blood Flow", *J. Nucl. Med.* 31: 885 (Abst).

Zubay, Geoffrey (1983). Biochemistry, Protein Structure and Function pp. 3–7, Published by Addison–Wesley Publishing Company, Inc.

Lister–James et al., "A Structure–Activity–Relationship (SAR) Study of Somatostatin Receptor–Binding Peptides Radiolabeled with TC–99m," *The Journal of Nuclear Medicine* 35(5), 257P–258P (1994) Abstract 1056.

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled peptides and methods for producing such peptides. Specifically, the invention relates to peptides, methods and kits for making such peptides, and methods for using such peptides to image sites in a mammalian body labeled with technetium-99m (Tc-99m) via a radiolabel-binding moiety covalently attached to a specific binding peptide via an amino acid side-chain of the peptide.

29 Claims, 1 Drawing Sheet

FOREIGN PATENT DOCUMENTS

| | | |
|---|---|---|
| WO9015818 | 12/1990 | WIPO . |
| WO9116919 | 11/1991 | WIPO . |
| WO9117173 | 11/1991 | WIPO . |
| WO9213572 | 8/1992 | WIPO . |
| WO9310747 | 6/1993 | WIPO . |
| WO9317719 | 9/1993 | WIPO . |
| WO9321962 | 11/1993 | WIPO . |
| WO9323085 | 11/1993 | WIPO . |
| WO9325244 | 12/1993 | WIPO . |
| WO9400489 | 1/1994 | WIPO . |
| 9500553 | 1/1995 | WIPO . |
| 9503330 | 2/1995 | WIPO . |
| 9529708 | 11/1995 | WIPO . |
| 9531221 | 11/1995 | WIPO . |

TECHNETIUM-99M LABELED PEPTIDES FOR IMAGING

This application is a continuation-in-part of U.S. patent application Ser. No. 07/653,012, filed Feb. 8, 1991 and now abandoned; this application is also a continuation-in-part of U.S. patent application Ser. No. 08/092,355, filed Jul. 15, 1993.

BACKGROUND OF THE INVENTION

1. Field of the Invention

This invention relates to radiodiagnostic reagents and peptides, and methods for producing labeled radiodiagnostic agents. Specifically, the invention relates to peptides, methods and kits for making such peptides, and methods for using such peptides to image sites in a mammalian body labeled with technetium-99m (Tc-99m) via a radiolabel-binding moiety which forms a neutral complex with Tc-99m.

2. Description of the Prior Art

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including $^{67}$Ga, $^{99m}$Tc (Tc-99m), $^{111}$In, $^{123}$I, $^{125}$I, and $^{169}$Yb. Tc-99m is a preferred radionuclide because it emits gamma radiation at 140 keV, it has a physical half-life of 6 hours, and it is readily available on-site using a molybdenum-99/technetium-99m generator.

The sensitivity of imaging methods using radioactively-labeled peptides is much higher than other radiopharmaceuticals known in the art, since the specific binding of the radioactive peptide concentrates the radioactive signal over the area of interest. Small synthetic peptides that bind specifically to targets of interest may be advantageously used as the basis for radiotracers. This is because: 1. they may be synthesized chemically (as opposed to requiring their production in a biological system such as bacteria or mammalian cells, or their isolation from a biologically-derived substance such as a fragment of a protein); 2. they are small, hence non-target bound radiotracer is rapidly eliminated from the body, thereby reducing background (non-target) radioactivity and allowing good definition of the target; and 3. small peptides may be readily manipulated chemically to optimize their affinity for a particular binding site.

Small readily synthesized labeled peptide molecules are preferred as routinely-used radiopharmaceuticals. There is clearly a need for small synthetic labeled peptides that can be directly injected into a patient and will image pathological sites by localizing at such sites. Tc-99m labeled small synthetic peptides offer clear advantages as radiotracers for gamma scintigraphy, due to the properties of Tc-99m as a radionuclide for imaging and the utility of specific-binding small synthetic peptides as radiotracer molecules.

Radiolabeled peptides have been reported in the prior art.

Ege et al., U.S. Pat. No. 4,832,940 teach radiolabeled peptides for imaging localized T-lymphocytes.

Olexa et al., 1982, European Patent Application No. 823017009 disclose a pharmaceutically acceptable radiolabeled peptide selected from Fragment $E_1$ isolated from cross-linked fibrin, Fragment $E_2$ isolated from cross-linked fibrin, and peptides having an amino acid sequence intermediate between Fragments $E_1$ and $E_2$.

Ranby et al., 1988, PCT/US88/02276 disclose a method for detecting fibrin deposits in an animal comprising covalently binding a radiolabeled compound to fibrin.

Hadley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Lees et al., 1989, PCT/US89/01854 teach radiolabeled peptides for arterial imaging.

Sobel, 1989, PCT/US89/02656 discloses a method to locate the position of one or more thrombi in an animal using radiolabeled, enzymatically inactive tissue plasminogen activator.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Maraganore et al., 1991, PCT/US90/04642 disclose a radiolabeled thrombus inhibitor comprising (a) a inhibitor moiety; (b) a linker moiety; and (c) and anion binding site moiety.

Rodwell et al., 1991, PCT/US91/03116 disclose conjugates of "molecular recognition units" with "effector domains".

Tubis et al., 1968, Int. J. Appl. Rad. Isot. 19: 835–840 describe labeling a peptide with technetium-99m.

Sundrehagen, 1983, Int. J. Appl. Rad. Isot. 34: 1003 describes labeling polypeptides with technetium-99m.

The use of chelating agents for radiolabeling polypeptides, and methods for labeling peptides and polypeptides with Tc-99m are known in the prior art and are disclosed in co-pending U.S. patent applications Ser. Nos. 07/653,012 now abandoned and 07/807,062, now U.S. Pat. No. 5,443,815 which are hereby incorporated by reference.

Although optimal for radioimaging, the chemistry of Tc-99m has not been as thoroughly studied as the chemistry of other elements and for this reason methods of radiolabeling with technetium are not abundant. Tc-99m is normally obtained as Tc-99m pertechnetate (TcO$_4^-$; technetium in the +7 oxidation state), usually from a molybdenum-99/ technetium-99m generator. However, pertechnetate does not bind well to other compounds. Therefore, in order to radiolabel a peptide, Tc-99m pertechnetate must be converted to another form. Since technetium does not form a stable ion in aqueous solution, it must be held in such solutions in the form of a coordination complex that has sufficient kinetic and thermodynamic stability to prevent decomposition and resulting conversion of Tc-99m either to insoluble technetium dioxide or back to pertechnetate.

Such coordination complexes of Tc-99m (in the +1 to +6 oxidation states) are known. However, many of these complexes are inappropriate for radiolabeling due to the molecular geometry of the coordination complex. For the purpose of radiolabeling, it is particularly advantageous for the coordination complex to be formed as a chelate in which all of the donor groups surrounding the technetium ion are provided by a single chelating ligand. This allows the chelated Tc-99m to be covalently bound to a peptide through a single linker between the chelator and the peptide.

These ligands are sometimes referred to as bifunctional chelating agents having a chelating portion and a linking portion. Such compounds are known in the prior art.

Byrne et al., U.S. Pat. No. 4,434,151 describe homocysteine thiolactone-derived bifunctional chelating agents that can couple radionuclides to terminal amino-containing compounds that are capable of localizing in an organ or tissue to be imaged.

Fritzberg, U.S. Pat. No. 4,444,690 describes a series of technetium-chelating agents based on 2,3-bis (mercaptoacetamido) propanoate.

Byrne et al., U.S. Pat. No. 4,571,430 describe novel homocysteine thiolactone bifunctional chelating agents for chelating radionuclides that can couple radionuclides to terminal amino-containing compounds that are capable of localizing in an organ or tissue to be imaged.

Byrne et al., U.S. Pat. No. 4,575,556 describe novel homocysteine thiolactone bifunctional chelating agents for chelating radionuclides that can couple radionuclides to terminal amino-containing compounds that are capable of localizing in an organ or tissue to be imaged.

Davison et al., U.S. Pat. No. 4,673,562 describe technetium chelating complexes of bisamido-bisthio-ligands and salts thereof, used primarily as renal function monitoring agents.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Fritzberg et al., European Patent Application No. 86100360.6 describe dithiol, diamino, or diamidocarboxylic acid or amine complexes useful for making technetium-labeled imaging agents.

Dean et al., 1989, PCT/US89/02634 describe bifunctional coupling agents for radiolabeling proteins and peptides.

Flanagan et al., European Patent Application No. 90306428.5 disclose Tc-99m labeling of synthetic peptide fragments via a set of organic chelating molecules. Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Dean, co-pending U.S. patent application Ser. No. 07/653, 012 now abandoned teaches reagents and methods for preparing peptides comprising a Tc-99m chelating group covalently linked to a specific binding peptide for radioimaging in vivo, and is hereby incorporated by reference.

Baidoo & Lever, 1990, Bioconjugate Chem. 1: 132–137 describe a method for labeling biomolecules using a bisamine bisthiol group that gives a cationic technetium complex.

It is possible to radiolabel a peptide by simply adding a thiol-containing moiety such as cysteine or mercaptoacetic acid. Such procedures have been described in the prior art.

Schochat et al., U.S. Pat. No. 5,061,641 disclose direct radiolabeling of proteins comprised of at least one "pendent" sulfhydryl group.

Dean et al., co-pending U.S. patent application Ser. No. 07/807,062 now U.S. Pat. No. 5,443,815 teach radiolabeling peptides via attached groups containing free thiols, and is incorporated herein by reference.

Goedemans et al., PCT Application No. WO 89/07456 describe radiolabeling proteins using cyclic thiol compounds, particularly 2-iminothiolane and derivatives.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes Tc-99m labeling of RGD-containing oligopeptides.

Burns et al., 1985, European Patent Application 85104959.3 describe bisamine bisthiol compounds for making small neutral Tc-99m brain imaging agents.

Kung et al., 1986, European Patent Application 86105920.2 describe bisamine bisthiol compounds for making small neutral Tc-99m imaging agents.

Bergstein et al., 1988, European Patent Application 88102252.9 describe bisamine bisthiol compounds for making small neutral Tc-99m brain imaging agents.

Bryson et al., 1988, Inorg. Chem. 27: 2154–2161 describe neutral complexes of technetium-99 which are unstable to excess ligand.

Misra et al., 1989, Tet. Let. 30: 1885–1888 describe bisamine bisthiol compounds for radiolabeling purposes.

Bryson et al., 1990, Inorg. Chem. 29: 2948–2951 describe chelators containing two amide groups, a thiol group and a substituted pyridine that may form neutral Tc-99 complexes.

Taylor et al., 1990, J. Nucl. Med. 31: 885 (Abst) describe a neutral Tc-99m complex for brain imaging.

The use of chelating agents for radiolabeling peptides, and methods for labeling peptides with Tc-99m are known in the prior art and are disclosed in co-pending U.S. patent application Ser. Nos. 07/653,012, now abandoned, a divisional of which issued as U.S. Pat. No. 5,654,272; 07/807, 062, now U.S. Pat. No. 5,443,815; 07/871,282, a divisional of which issued as U.S. Pat. No. 5,780,007; 07/886,752, now abandoned, a divisional of which issued as U.S. Pat. No. 5,736,122; 07/893,981, now U.S. Pat. No. 5,508,020; 07/955,466; 08/019,864, now U.S. Pat. No. 5,552,525; 08/073,577, now U.S. Pat. No. 5,561,220; 08/210,822, now abandoned; 08/236,402; and 08/241,625, now U.S. Pat. No. 5,783,170; (Attorney Docket No. 91,875-C), and radiolabeled peptides for use as scintigraphic imaging agents for imaging thrombi are known in the prior art and are disclosed in co-pending U.S. patent application Ser. Nos. 07/886,752, 07/893,981 and 08/044,825 and International Patent Applications Serial Nos. PCT/US92/00757, PCT/US92/10716, PCT/US93/02320, PCT/US93/03687, PCT/US93/04794, PCT/US93/05372, PCT/US93/06029, PCT/US93/09387, PCT/US94/01894, PCT/US94/03878 (Attorney Docket No. 90,1104-L), and PCT/US94/05895 (Attorney Docket No. 90,1104-N), each of which are hereby incorporated by reference in its entirety.

SUMMARY OF THE INVENTION

The present invention provides scintigraphic imaging agents that are radioactively-labeled peptides. The radiolabeled peptides of the invention are comprised of peptides that specifically bind to a target in vivo and are covalently linked to a radiolabel-binding moiety wherein the moiety binds a radioisotope. It is a particular advantage in the present invention that the radiolabel-binding moiety is covalently linked to a side-chain of an amino acid residue comprising the peptide.

This mode of covalent linkage is advantageous for a number of reasons. First, covalent linkage to a side-chain of an amino acid constituent of the peptide avoids interference of the covalently linked radiolabel binding moiety with the specific binding properties of the specific binding peptide. Second, this arrangement permits cyclic peptides, which by definition not comprised of free amino or carboxy termini, to be used in conjunction with radiolabel binding moieties to be useful as scintigraphic imaging agents as disclosed here. Third, covalent linkage to the sidechain of a constituent amino acid permits each of the scintigraphic imaging agents of the invention to be more flexibly designed to achieve optimal increases efficacy and reductions in antigenicity, etc. Conjugation to an amino acid side-chain also allows the radiolabel binding moiety to be added to the peptide during synthesis as an amino acid conjugate, or after synthesis of the completed peptide has been achieved. Lastly, cyclic peptides are known to be resistant to exoprotease digestion, thereby incorporating the improved stability of such peptides in vivo into the scintigraphic imaging agents of the invention.

In a first aspect of the present invention, radiolabeled peptides are provided capable of imaging sites within a mammalian body. The peptides are comprised of a specific binding peptide having an amino acid sequence and a radiolabel-binding moiety covalently linked to the peptide. Further, the radiolabel-binding moiety is covalently linked to a side-chain of an amino acid comprising the peptide. In a preferred embodiment, the radiolabel-binding moiety is covalently linked to the side-chain of an amino acid having a side-chain comprising an amine or a thiol, the amino acid being most preferably lysine or homocysteine. In another preferred embodiment, the radiolabel is technetium-99m.

One aspect of the invention provides a reagent for preparing a scintigraphic imaging agent for imaging sites within a mammalian body, comprising a specific binding peptide wherein a radiolabel binding moiety is covalently linked to the peptide via an amino acid side-chain of an amino acid of the peptide, the radiolabel binding moiety having the formula:

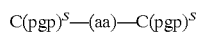

$$C(pgp)^S - (aa) - C(pgp)^S \qquad \text{I.}$$

wherein $C(pgp)^S$ is a protected cysteine and (aa) is any primary α- or β-amino acid not containing a thiol group. In a preferred embodiment, the amino acid is glycine.

In another embodiment, the invention provides a reagent for preparing a scintigraphic imaging agent for imaging sites within a mammalian body, comprising a specific binding peptide wherein a radiolabel binding moiety is covalently linked to the peptide via an amino acid side-chain of an amino acid of the peptide, the radiolabel binding moiety comprising a single thiol having the formula:

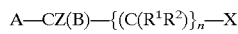

$$A - CZ(B) - \{(C(R^1R^2)\}_n - X \qquad \text{II.}$$

wherein A is H, HOOC, $H_2NOC$, (amino acid or peptide)-NHOC, (amino acid or peptide)-OOC or $R^4$; B is H, SH or $-NHR^3$, $-N(R^3)$-(amino acid or peptide) or $R^4$; Z is H or $R^4$; X is SH or $-NHR^3$, $-N(^3)$-(amino acid or peptide) or $R^4$; $R^1$, $R^2$, $R^3$ and $R^4$ are independently H or straight or branched chain or cyclic lower alkyl; n is 0, 1 or 2; wherein (peptide) is a peptide of 2 to about 10 amino acids; and: (1) where B is $-NHR^3$ or $-N(R^3)$-(amino acid or peptide), X is SH and n is 1 or 2; (2) where X is $-NHR^3$ or $-N(R^3)$-(amino acid or peptide), B is SH and n is 1 or 2; (3) where B is H or $R^4$, A is HOOC, $H_2NOC$, (amino acid or peptide)-NHOC, (amino acid or peptide)-OOC, X is SH and n is 0 or 1; (4) where A is H or $R^4$, then where B is SH, X is $-NHR^3$ or $-N(R^3)$-(amino acid or peptide) and where X is SH, B is $-NHR^3$ or $-N(R^3)$-(amino acid or peptide); (5) where X is H or $R^4$, A is HOOC, $H_2NOC$, (amino acid or peptide)-NHOC, (amino acid or peptide)-OOC and B is SH; (6) where Z is methyl, X is methyl, A is HOOC, $H_2NOC$, (amino acid or peptide)-NHOC, (amino acid or peptide)-OOC and B is SH and n is 0; and wherein the thiol moiety is in the reduced form and wherein (amino acid) is any primary α- or β-amino acid not containing a thiol group.

In particular embodiments of this aspect of the invention, the radiolabel-binding moiety has a formula that is:

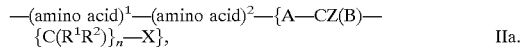

—(amino acid)$^1$—(amino acid)$^2$—{A—CZ(B)—
{C(R$^1$R$^2$)}$_n$—X}, \qquad IIa.

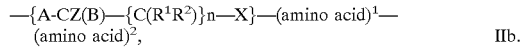

—{A-CZ(B)—{C(R$^1$R$^2$)}n—X}—(amino acid)$^1$—
(amino acid)$^2$, \qquad IIb.

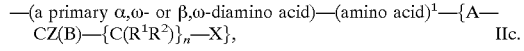

—(a primary α,ω- or β,ω-diamino acid)—(amino acid)$^1$—{A—
CZ(B)—{C(R$^1$R$^2$)}$_n$—X}, \qquad IIc.

or

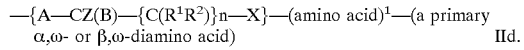

—{A—CZ(B)—{C(R$^1$R$^2$)}n—X}—(amino acid)$^1$—(a primary
α,ω- or β,ω-diamino acid) \qquad IId.

wherein (amino acid)$^1$ and (amino acid)$^2$ are each independently any naturally-occurring, modified, substituted or altered α- or β-amino acid not containing a thiol group; A is H, HOOC, $H_2NOC$, (amino acid or peptide)-NHOC, (amino acid or peptide)-OOC or $R^4$; B is H, SH or $-NHR^3$, $-N(R^3)$-(amino acid or peptide) or $R^4$; Z is H or $R^4$; X is SH or $-NHR^3$, $-N(R^3)$-(amino acid or peptide) or $R^4$; $R^1$, $R^2$, $R^3$ and $R^4$ are independently H or straight or branched chain or cyclic lower alkyl; n is an integer that is either 0, 1 or 2; (peptide) is a peptide of 2 to about 10 amino acids; and: (1) where B is $-NHR^3$ or $-N(R^3)$-(amino acid or peptide), X is SH and n is 1 or 2; (2) where X is $-NHR^3$ or $-N(R^3)$-(amino acid or peptide), B is SH and n is 1 or 2; (3) where B is H or $R^4$, A is HOOC, $H_2NOC$, (amino acid or peptide)-NHOC, (amino acid or peptide)-OOC, X is SH and n is 0 or 1; (4) where A is H or $R^4$, then where B is SH, X is $-NHR^3$ or $-N(R^3)$-(amino acid or peptide) and where X is SH, B is $-NHR^3$ or $-N(R^3)$-(amino acid or peptide); (5) where X is H or $R^4$, A is HOOC, $H_2NOC$, (amino acid or peptide)-NHOC, (amino acid or peptide)-OOC and B is SH; (6) where Z is methyl, X is methyl, A is HOOC, $H_2NOC$, (amino acid or peptide)-NHOC, (amino acid or peptide)-OOC and B is SH and n is 0; and; and wherein the thiol group is in the reduced form.

In another embodiment, the invention provides a radiolabeled peptide for imaging sites within a mammalian body, comprising a specific binding peptide wherein a radiolabel binding moiety is covalently linked to the peptide via an amino acid side-chain of an amino acid of the peptide, the radiolabel binding moiety having the formula:

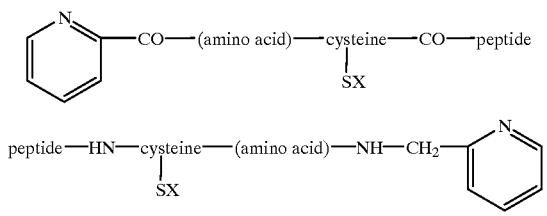

{for purposes of this invention, radiolabel-binding moieties having this structure will be referred to as picolylamine (Pica)-based moieties}
wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the peptide is covalently linked to the radiolabel-binding moiety via an amino acid, most preferably glycine, and the radiolabel is technetium-99m.

In yet another embodiment of the invention, a radiolabeled peptide is provided for imaging sites within a mammalian body, comprising a specific binding peptide and a bisamino bisthiol radiolabel-binding moiety covalently linked to the peptide via an amino acid side-chain of the peptide. The bisamino bisthiol radiolabel-binding moiety in this embodiment of the invention has a formula selected from the group consisting of:

I.

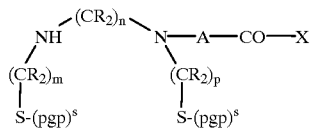

wherein each R can be independently H, $CH_3$ or $C_2H_5$; each $(pgp)^S$ can be independently a thiol protecting group or H; m, n and p are independently 2 or 3; A is linear or cyclic lower alkyl, aryl, heterocyclyl, combinations or substituted derivatives thereof; and X is peptide; and

II.

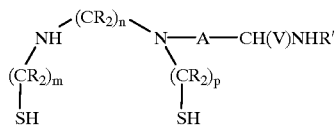

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. [For purposes of this invention, radiolabel-binding moieties having these structures will be referred to as "BAT" moieties]. In a preferred embodiment, the peptide is covalently linked to the radiolabel-binding moiety via an amino acid, most preferably glycine, and the radiolabel is technetium-99m.

In preferred embodiments of the aforementioned aspects of this invention, the specific binding compound is a peptide is comprised of between 3 and 100 amino acids. The most preferred embodiment of the radiolabel is technetium-99m.

Specific-binding peptides provided by the invention include but are not limited to peptides having the following sequences:
formyl-MLF
(VGVAPG)₃amide
(VPGVG)₄amide
RALVDTLKFVTQAEGAKamide (SEQ ID NO:1)
RALVDTEFKVKQEAGAKamide (SEQ ID NO:2)
PLARITLPDFRLPEIAIPamide (SEQ ID NO:3)
GQQHHLGGAKAGDV (SEQ ID NO:4)
PLYKKIIKKLLES (SEQ ID NO:5)
LRALVDTLKamide (SEQ ID NO:6)
GGGLRALVDTLKamide (SEQ ID NO:7)
GGGLRALVDTLKFVTQAEGAKamide (SEQ ID NO:8)
GGGRALVDTLKALVDTLamide (SEQ ID NO:9)
GHRPLDKKREEAPSLRPAPPPISGGGYR (SEQ ID NO:10)
PSPSPIHPAHHKRDRRQamide (SEQ ID NO:11)
GGGF_D.Cpa.YW_D.KTFamide (SEQ ID NO.: 12)

[SYNRGDSTC]₃-TSEA
GGGLRALVDTLKamide (SEQ ID.:13)
GCGGGLRALVDTLKamide (SEQ ID.:14)
GCYRALVDTLKFVTQAEGAKamide (SEQ ID.:15)
GC(VGVAPG)₃amide The reagents of the invention may be formed wherein the specific binding peptides or the radiolabel-binding moieties are covalently linked to a polyvalent linking moiety. Polyvalent linking moieties of the invention are comprised of at least 2 identical linker functional groups capable of covalently bonding to specific binding compounds or radiolabel-binding moieties. Preferred linker functional groups are primary or secondary amines, hydroxyl groups, carboxylic acid groups or thiol-reactive groups. In preferred embodiments, the polyvalent linking moieties are comprised of bis-succinimdylmethylether (BSME), 4-(2,2-dimethylacetyl)benzoic acid (DMAB), tris (succinimidylethyl)amine (TSEA), N{2-(N',N'-bis(2-succinimidoethyl)aminoethyl)}-N⁶,N₉-bis(2-methyl-2-mercaptopropyl)-6,9-diazanonanamide (BAT-BS), bis-(acetamidoethyl)ether, tris(acetamidoethyl)amine, bis-(acetamidoethyl)ether, bis-(acetamidomethyl)ether, α,ε-bisacetyllysine, lysine and 1,8-bis-acetamido-3,6-dioxaoctane.

The invention also comprises complexes of the peptides of the invention with Tc-99m and methods for radiolabeling the peptides of the invention with Tc-99m. Radiolabeled complexes provided by the invention are formed by reacting the peptides of the invention with Tc-99m in the presence of a reducing agent. Preferred reducing agents include but are not limited to dithionite ion, stannous ion, and ferrous ion. Complexes of the invention are also formed by labeling the peptides of the invention with Tc-99m by ligand exchange of a prereduced Tc-99m complex as provided herein.

The invention also provides kits for preparing the peptides of the invention radiolabeled with Tc-99m. Kits for labeling the peptide of the invention with Tc-99m are comprised of a sealed vial containing a predetermined quantity of a peptide of the invention and a sufficient amount of reducing agent to label the peptide with Tc-99m.

This invention provides methods for preparing peptides of the invention by chemical synthesis in vitro. In a preferred embodiment, peptides are synthesized by solid phase peptide synthesis.

This invention provides methods for using Tc-99m labeled peptides for imaging a site within a mammalian body by obtaining in vivo gamma scintigraphic images. These methods comprise administering an effective diagnostic amount of a Tc-99m radiolabeled peptide of the invention and detecting the gamma radiation emitted by the Tc-99m localized at the site within the mammalian body.

Specific preferred embodiments of the present invention will become evident from the following more detailed description of certain preferred embodiments and the claims.

DETAILED DESCRIPTION OF THE INVENTION

Figure 1:
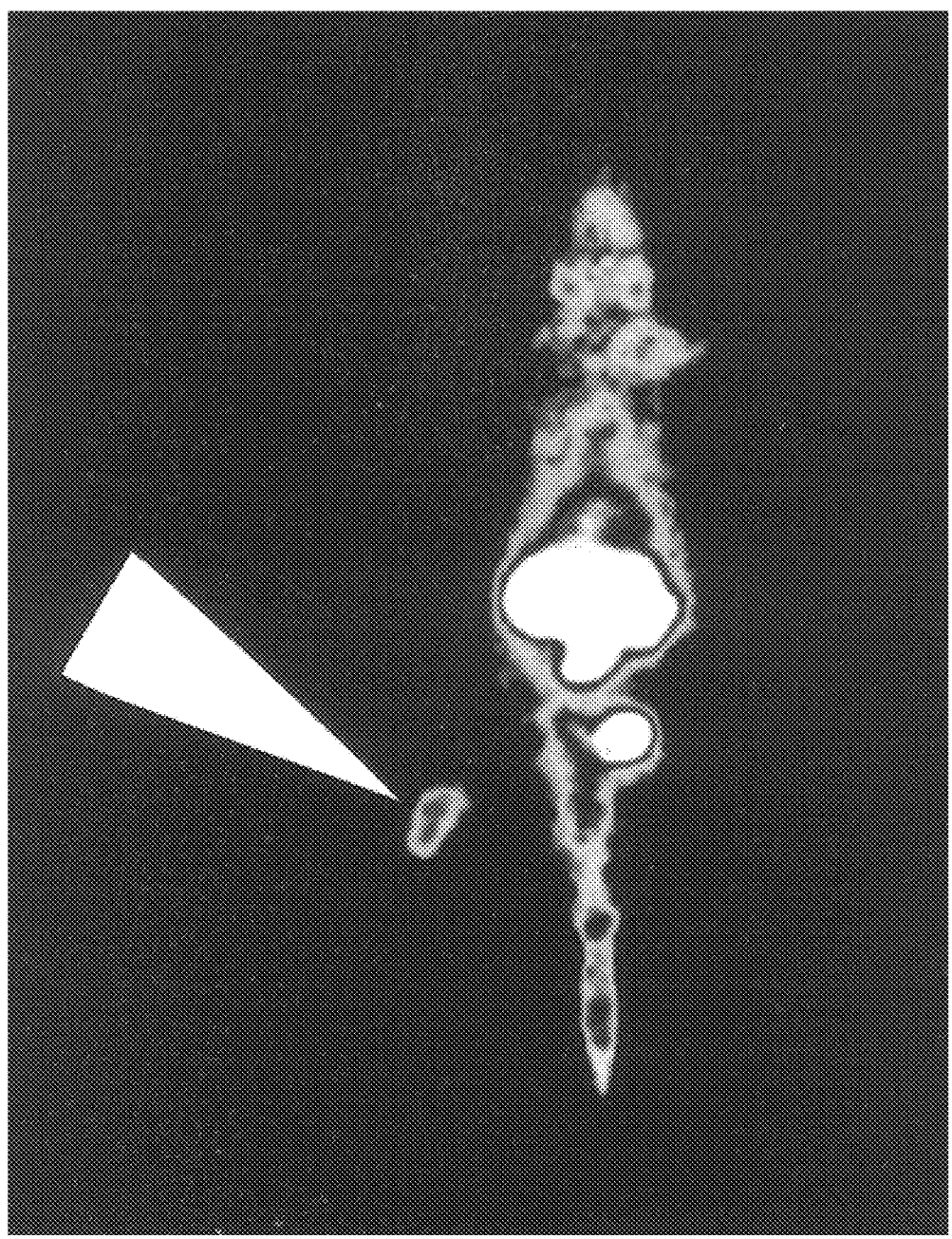
FIG. 1 shows an image of $^{99m}$Tc-P587 in a tumor-bearing rat.

The present invention provides Tc-99m labeled peptides for imaging target sites within a mammalian body comprising an amino acid sequence covalently linked through an amino acid side-chain to a radiolabel-binding moiety wherein the radiolabel-binding moiety binds a radioisotope.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

In the radiolabel binding moieties and peptides covalently linked to such moieties that contain a thiol covalently linked to a thiol protecting groups [(pgp)$^S$] provided by the invention, the thiol-protecting groups may be the same or different and may be but are not limited to:

—CH$_2$-aryl (aryl is phenyl or alkyl or alkyloxy substituted phenyl);
—CH-(aryl)$_2$, (aryl is phenyl or alkyl or alkyloxy substituted phenyl);
—C-(aryl)$_3$, (aryl is phenyl or alkyl or alkyloxy substituted phenyl);
—CH$_2$-(4-methoxyphenyl);
—CH-(4-pyridyl)(phenyl)$_2$;
—C(CH$_3$)$_3$
-9-phenylfluorenyl;
—CH$_2$NHCOR (R is unsubstituted or substituted alkyl or aryl);
—CH$_2$—NHCOOR (R is unsubstituted or substituted alkyl or aryl);
—CONHR (R is unsubstituted or substituted alkyl or aryl);
—CH$_2$—S—CH$_2$-phenyl Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D- amino acids, naturally occurring and otherwise.

Peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

It is a particular advantage of the present invention that a radiolabel-binding moiety is covalently linked to the peptide via an amino acid side-chain of the target specific binding peptide. This may be accomplished by either coupling the radiolabel binding moiety to the peptide by formation of a covalent bond with a particular amino acid side-chain or through incorporation of an amino acid conjugated to a radiolabel-binding moiety during peptide synthesis.

In the former case, for example, the radiolabel-binding moiety ClCH$_2$CO.Gly-Gly-Cys-Lys.amide (SEQ ID NO.:16) (protected during synthesis, inter alia, by tritylation of the thiol group of the cysteine residue) is coupled at pH 8–10 to the somatostatin receptor binding peptide cyclo.(N—CH$_2$).Phe-Tyr-(D-Trp)-Lys-Val-Hcy to form the peptide cyclo.(N—CH$_2$).Phe-Tyr-(D-Trp)-Lys-Val-Hcy.(CH$_2$CO).Gly-Gly-Cys-Lys.amide (following de-protection). In this formula, it will be understood that the radiolabel-binding moiety is covalently linked to the sidechain sulfur atom of homocysteine.

Alternatively, the radiolabel-binding moiety BAT (N$^6$,N$^9$-bis(2-mercapto-2-methylpropyl)-6,9-diazanonanoic acid) is incorporated into the leukocyte binding peptide formyl.Met-Leu-Phe-Lys.amide by using the prepared lysine derivative, Nα(Fmoc)-Nε(N$^9$-(t-butoxycarbonyl)-N$^6$,N$^9$-bis(2-methyl-2-triphenylmethylthiopropyl)-6,9-diazanonanoyl)lysine during peptide synthesis.

Other radiolabel binding moieties of the invention may be introduced into the target specific peptide during peptide synthesis. The picolinic acid-containing radiolabel-binding moiety may be covalently linked to the ε-amino group of lysine to give, for example, αN(Fmoc)-Lys-εN[Pic-Gly-Cys (protecting group)], which may be incorporated at any position in the peptide chain. This sequence is particularly advantageous as it affords an easy mode of incorporation into the target binding peptide.

In forming a complex of radioactive technetium with the peptides of this invention, the technetium complex, preferably a salt of Tc-99m pertechnetate, is reacted with the peptides of this invention in the presence of a reducing agent. Preferred reducing agents are dithionite, stannous and ferrous ions; the most preferred reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of a peptide of the invention to be labeled and a sufficient amount of reducing agent to label the peptide with Tc-99m. Alternatively, the complex may be formed by reacting a peptide of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 3 and 100 amino acid residues, and are covalently linked to a radiolabel-binding moiety wherein the radiolabel-binding moiety binds a radioisotope. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 3 hereinbelow.

Radioactively labeled peptides provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Technetium-labeled peptides provided by the present invention can be used for visualizing sites in a mammalian body. In accordance with this invention, the technetium-labeled peptides are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the organ or tumor in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxy-methylpolystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

Where appropriate αN-formyl groups were introduced by treating the cleaved, deprotected peptide with excess acetic anhydride in 98% formic acid and stirring for about 18 hours followed by HPLC purification. Where appropriate N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-haloacetic acid as the last residue to be coupled during SPPS or by treating the N-terminus free amino peptide bound to the resin with either the 2-haloacetic acid/diisopropylcarbodiimide/N-hydroxysuccinimide in NMP of the 2-halo-acetic anhydride/diisopropylethylamine in NMP. Where appropriate, HPLC-purified 2-haloacetylated peptides were cyclized by stirring an 0.1–1.0 mg/mL solution in bicarbonate or ammonia buffer (pH 8) with or without 0.5–1.0 mM EDTA for 1–48 hours, followed by acidification with acetic acid, lyophilization and HPLC purification. Where appropriate, Cys-Cys disulfide bond cyclizations were performed by treating the precursor cysteine-free thiol peptides at 0.1 mg/mL in pH 7 buffer with aliquots of 0.006 M $K_3Fe(CN)_6$ until a stable yellow color persisted. The excess oxidant was reduced with excess cysteine, the mixture was lyophilized and then purified by HPLC.

Where appropriate the "Pica"' group was introduced by conjugating picolylamine to a precursor peptide using diisopropylcarbodiimide and N-hydroxysuccinimide. Where appropriate BAT ligands were introduced either by using the appropriate BAT acid as the last residue to be coupled during SPPS or by treating the N-terminus free amino peptide bound to the resin with BAT acid/ diisopropylcarbodiimide/ N-hydroxysuccinimide in NMP. Where appropriate, [BAM] was conjugated to the peptide by first activating the peptide carboxylate with a mixture of diisopropylcarbodiimide/N-hydroxysuccinimide or HBTU/HOBt in DMF, NMP or $CH_2Cl_2$, followed by coupling in the presence of diisopropylethylamine; after coupling, the conjugate was deprotected as described above.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/ acetonitrile or THF) with 0.33 molar equivalents of TMEA (tris(2-maleimidoethyl)amine; as disclosed in U.S. Ser. No. 08/044,825, incorporated by reference) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-[2-(N',N'-bis(2-maleimidoethyl)aminoethyl)]-$N^9$-(t-butoxycarbonyl)-$N^6$,$N^9$,-bis(2-methyl-2-triphenylmethylthiopropyl)-6,9-diazanonanamide; as disclosed in U.S. Ser. No. 08/044,825, incorporated by reference) pre-dissolved in acetonitrile or THF, at room temperature for approximately 1–18h. The solution was then evaporated to dryness and [BAT-BS]-peptide conjugates deprotected by treatment with 10 mL TFA and 0.2 mL triethylsilane for 1 h. The solution was concentrated, the product adducts precipitated with ether, and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m 0.1 mg of a peptide prepared as in Example 1 was dissolved in 0.1 mL of water or 50 mM potassium phosphate buffer (pH=5, 6 or 7.4). Tc-99m gluceptate was prepared by reconstituting a Glucoscan vial (E. I. DuPont de Nemours, Inc.) with 1.0 mL of Tc-99m sodium pertechnetate containing up to 200 mCi and allowed to stand for 15 minutes at room temperature. 25 µl of Tc-99m gluceptate was then added to the peptide and the reaction allowed to proceed at room temperature or at 100° C. for 15–30 min and then filtered through a 0.2 µm filter.

The Tc-99m labeled peptide purity was determined by HPLC using the following conditions: a Waters DeltaPure RP-18, 5µ, 150 mm×3.9 mm analytical column was loaded with each radiolabeled peptide and the peptides eluted at a solvent flow rate equal to 1 mL/min. Gradient elution was performed beginning with 10% solvent A (0.1% CF3COOH/$H_2O$) to 40% solvent $B_{90}$ (0.1% $CF_3COOH$/90% $CH_3CN$/$H_2O$) over the course of 20 min.

Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Tables illustrates successful Tc-99m labeling of peptides prepared according to Example 1 using the method described herein.

TABLE I

| Peptides | FABMS MH+ | Radiochemical Yield(%)* | HPLC $R_T$(min) |
|---|---|---|---|
| cyclo(N-methyl)FYW_D_KV.Hcy.(CH_2CO.GGC.amide) | 1129 | 98[2] | 15.1, 17.2 |
| cyclo(N-methyl)FYW_D_KV.Hcy.(CH_2CO.GGCK.amide) | 1258 | 99[2] | 15.0 |
| cyclo(N-methyl)FYW_D_KV.Hcy.(CH_2CO.GGCR.amide) | 1285 | 99[1] | 15.1 |
| cyclo(N-methyl)FYW_D_KV.Hcy.(CH_2CO.GGCKK.amide) | 1386 | N.D. | N.D. |
| cyclo(N-methyl)FYW_D_KV.Hcy.(CH_2CO.GGC.Orn.amide) | 1244 | 98[3] | 7.0 |

*Superscripts refer to the following labeling conditions:
[1]= in 10% HPCD at room temperature
[2]= in 50/50 ethanol/water at room temperature
[3]= in 0.9% NaCl at 100° C.
HPLC methods (indicated by superscript after $R_T$):
Waters-1 column, 100% Solution A → 100% Solution B in 10 min

TABLE II

| Peptides | FABMS MH+ | Radiochemical Yield(%)* | HPLC $R_T$(min) |
|---|---|---|---|
| formyl-MLFK.(BAT).amide (SEQ ID NO.: 17) | 884 | 99 | 12.6 |
| formyl-MLFK.(BAT) (SEQ ID NO.: 17) | 884 | 96 | 11.9, 12.8 |
| formyl-MLFK.(BAT).KKKKK.amide (SEQ ID NO.: 18) | 1524 | 96 | 11.7, 12.2 |
| formyl-MLFK.(BAT).GSGSGS.amide (SEQ ID NO.: 19) | 1315 | 97 | 11.9, 12.8 |
| formyl-MLFK.(BAT).E (SEQ ID NO.: 20) | 1013 | 99 | 12.3 |
| formyl-MLFK.(BAT).EGE (SEQ ID NO.: 21) | 1200 | 98 | 13.7 |
| formyl-MLFK.(BAT).GGC_Acm_GC_Acm_GGC.amide)_2-BSME | 3477 | 99 | 11.9, 12.4 |

TABLE II-continued

| Peptides | FABMS MH+ | Radiochemical Yield(%)* | HPLC R$_T$(min) |
|---|---|---|---|
| YRALVDTLKFVTQAEGAK.(BAT).amide (SEQ ID NO.: 22) | 2329 | 98 | 11.4 |
| K.(BAT).D-Nal.C$_{Me}$YW$_D$KVC$_{Me}$T.amide | 1573 | 97 | 12.0, 12.5 |
| (DTPA).{D-Nal.SYW$_D$KVTK.(BAT)}$_2$.amide | 3210 | 97 | 12.1, 12.5 |
| (DTPA).{D-Nal.SYW$_D$KVTK.(BAT)}.amide | 1801 | 96 | 11.8, 12.0 |
| (DTPA)K.(BAT).D-Nal.C$_{Me}$YW$_D$KVC$_{Me}$T.amide | 1949 | 96 | 11.8, 12.0 |
| pGlu.GVNDNEEGFFSARK.(BAT).amide (SEQ ID NO.: 23) | 1997 | N.D. | N.D. |

The following labeling conditions were used with the appropriate peptides:
1. The peptide is dissolved in 50 mM potassium phosphate buffer (pH 7.4) and labeled at room temperature.
2. The peptide is dissolved in 50 mM potassium phosphate buffer (pH 7.4) and labeled at 100° C.
3. The peptide is dissolved in water and labeled at room temperature.
4. The peptide is dissolved in water and labeled at 100° C.
5. The peptide is dissolved in 50 mM potassium phosphate buffer (pH 6.0) and labeled at 100° C.
6. The peptide is dissolved in 50 mM potassium phosphate buffer (pH 5.0) and labeled at room temperature.
**HPLC methods:
general:
solvent A = 0.1% CF3COOH/H$_2$O
solvent B$_{70}$ = 0.1% CF$_3$COOH/70% CH$_3$CN/H$_2$O
solvent B$_{90}$ = 0.1% CF$_3$COOH/90% CH$_3$CN/H$_2$O
solvent flow rate = 1 mL/min
Vydak column = Vydak 218TP54 RP-18, 5$\mu$ × 220 mm × 4.6 mm analytical column with guard column
Brownlee column = Brownlee Spheri-5 RP-18, 5$\mu$ × 220 mm × 4.6 mm column
Waters column = Waters Delta-Pak C18, 5 $\mu$m, 39 × 150 mm
Method 1: Brownlee column    100% A to 100% B$_{70}$ in 10 min
Method 2: Vydak column    100% A to 100% B$_{90}$ in 10 min
Method 3: Vydak column    100% A to 100% B$_{70}$ in 10 min
Method 4: Brownlee column    100% A to 100% B90 in 10 min
Method 5: Waters column    100% A to 100% B$_{90}$ in 10 min Single-letter abbreviations for amino acids can be found in G. Zubay, *Biochemistry* (2d. ed.), 1988 (MacMillen Publishing: New York) p.33; Ac=acetyl; Pic=picolinoyl (pyridine-2-carbonyl)=6-aminocaproic acid; Hly=homolysine; Acm=acetamidomethyl; pGlu=pyro-glutamic acid; Mob=4-methoxybenzyl; Pica=picolylamine (2-(aminomethyl)pyridine); Apc=L-[S-(3-aminopropyl) cysteine; F$_D$=D-phenylalanine; W$_D$=D-tryptophan; Y$_D$=D-tyrosine; Cpa=L-(4-chlorophenyl)alanine; Thp=4-aminotetrahydrothiopyran-4-carboxylic acid; ma=mercaptoacetic acid; D-Nal=D-2-naphthylalanine; Dpg=dipropylglycine; Nle=norleucine; Hoy=homocysteine; BAT=N$^6$,N$^9$-bis(2-mercapto-2-methylpropyl)-6,9-diazanonanoic acid; BAT acid (protected)=N$^9$-(t-butoxycarbonyl)-N$^6$,N$^9$-bis(2-methyl-2-triphenylmethylthiopropyl)-6,9-diazanonanoic acid; BAM=N$^1$,N$^4$-bis(2-mercapto-2-methylpropyl)-1,4,10-triazadecane; BAM (protected)=N$^1$-(t-butoxycarbonyl)-N$^1$,N$^4$-bis(2-methyl-2-triphenylmethylthiopropyl)-1,4,10-triazadecane; [BAT-BM]=N-[2-(N',N'-bis(2-maleimidoethyl)aminoethyl]-N$^9$-(t-butoxycarbonyl)-N$^6$,N$^9$-bis(2-methyl- 2-triphenylmethylthiopropyl)-6,9-diazanonanamide; [BAT-BS]=N-[2-(N',N'-bis(2-succinimidoethyl)aminoethyl]-N$^6$,N$^9$-bis(2-mercapto-2-methylpropyl)-6,9-diazanonanamide; [BMME]=bis-maleimidomethylether; [BSME]=bis-succinimidomethylether; [DTPA]=diethylenetriaminepentaacetic acid.

EXAMPLE 3

Localization and In Vivo Imaging of Atherosclerotic Plaque using Tc-99m Labeled Compound P215 in the Hypercholesterol Rabbit Model Twenty-two New Zealand White (NZW) rabbits of both sexes and weighing 2–3 kg are divided into two groups. The control group of rabbits are housed and fed commercial rabbit chow (Purina). The HC group are fed a standardized, cholesterol-rich diet (rabbit chow mixed to a 1 % w/w concentration of cholesterol) from seven weeks until 28 weeks of age. All animals are given water ad libitum.

Tc-99m labeled P215 ({BAT}.RALVDTLKFVTQAEGAK.amide) (SEQ ID NO.:1) is prepared as described above in Example 1. Approximately 250–400 $\mu$g of peptide is labeled with 140–160 mCi of Tc-99m and prepared in unit doses of 7–8 mCi (12.5–20.0 $\mu$g/rabbit; 6–7 $\mu$g/kg) in 0.2 mL volume doses. Adult rabbits are dosed with Tc-99m labeled peptide intravenously in a lateral ear vein by slow bolus infusion (approximately 0.1 mL/min). A gamma camera fitted with a pin-hole collimator (5 mm aperture) and energy window set for Tc-99m and programmed to accumulate 500,000 counts or scan for a desired time is used to acquire images. Shortly before imaging, animals are anesthetized with a mixture of ketamine and xylazine (5:1, 1 mL/kg intramuscularly).

Gamma camera images are collected at 40°–45° just above the heart (left anterior oblique [LAO] view) to delineate the aortic arch and view the descending aorta. Images are acquired at 1 and 2 h and occasionally at 3 and 5 h after injection. Supplementary anesthesia is injected as needed prior to each image collection.

At 2.5 h (after a 2 h scan), animals are sacrificed with an intravenous dose of sodium pentobarbital. Upon necropsy, the aorta is removed and branching vessels dissected free from the aortic valve to the mid-abdominal region. Using a parallel hole collimator, the aorta is also imaged ex corpora. Next, the aortae are opened longitudinally and stained with Sudan IV, thereby turning atherosclerotic plaque a deep red brick color. Lipid-free and uninjured aortic endothelium retains its normal, glistening white-pink appearance under these conditions.

Positive correlations among the in vivo and ex corpora Tc-99m P215 images and the deposition patterns of Sudan IV in the HC-treated rabbit aortae indicate that this scintigraphic imaging agent of the invention is capable of imaging atherosclerotic plaque.

EXAMPLE 4

In Vivo Imaging using Tc-99m Labeled Compound P357 of Deep Vein Thrombosis in a Canine Model Mongrel dogs (25–35 lb., fasted overnight) are sedated with a combination of ketamine and aceprozamine intramuscularly and then anesthetized with sodium pentobarbital intravenously. An 18-gauge angiocath is inserted in the distal half of the right femoral vein and an 8 mm Dacron®-entwined stainless steel embolization coil (Cook Co., Bloomington Ind.) is placed in the femoral vein at approximately mid-femur in each animal. The catheter is removed, the wound sutured and the placement of the coil documented by X-ray. The animals are then allowed to recover overnight.

One day following coil placement, each animal is re-anesthetized, intravenous saline drips placed in each foreleg and a urinary bladder catheter inserted to collect urine. The animal is placed supine under a gamma camera which is equipped with a low-energy, all purpose collimator and photopeaked for Tc-99m. Images are acquired on a NucLear Mac computer system.

Tc-99m labeled P357 [($CH_2CO$-$Y_D$.Apc.GDCGGC$_{Acm}$GC$_{Acm}$GGC.amide)$_2$-[BAT-BS]] [185–370 mBq (5–10 mCi) Tc-99m and 0.2–0.4 mg P357] is injected into one foreleg intravenous line at its point of insertion. The second line is maintained for blood collection. Anterior images over the legs are acquired for 500,000 counts or 20 min (whichever was shorter), at approximately 10–20 min, and at approximately 1, 2, 3 and 4 h post-injection. Following the collection of the final image, each animal is deeply anesthetized with pentobarbital. Two blood samples are collected on a cardiac puncture using a heparinized syringe followed by a euthanasing dose of saturated potassium chloride solution administered by intercardiac or bolus intravenous injection. The femoral vein containing the thrombus and samples of thigh muscle are then carefully dissected out. The thrombus is then dissected free of the vessel and placed in a pre-weighed test tube. The thrombus samples are then weighed and counted in a gamma well counter in the Tc-99m channel. Known fractions of the injected doses are counted as well.

Fresh thrombus weight, percent injected dose (%ID)/g in the thrombus and blood obtained just prior to euthanasia and thrombus/blood and thrombus/muscle ratios are determined. Thrombus/background ratios are determined by analysis of the counts/pixel measured in regions-of-interest (ROI) drawn over the thrombus and adjacent muscle from computer-stored images.

These results are used to demonstrate that deep vein thrombi can be rapidly and efficiently located in vivo.

EXAMPLE 5

Scintigraphic Imaging and Biodistribution of Tc-99m Labeled Peptides

In order to demonstrate the effectiveness of Tc-99m labeled peptide reagents as provided above, New Zealand white rabbits were inoculated intramuscularly in the left calf with a potent stain of *E. coli*. After 24 h, the animals were sedated by i.m. injection of ketamine and xylazine, and then injected i.v. with Tc-99m labeled peptide ($\leq$150 μg, 2–10 mCi). The animals were positioned supine in the field of view of a gamma camera (LEAP collimator/ photopeaked for Tc-99m) and imaged over the first hour post-injection, and then at approximately 1 h intervals over the next three hours post injection. Animals were allowed to recover between image acquisitions and re-anesthetized as needed.

Upon completion of the final imaging, each animal was sacrificed by overdose of phenobarbital i.v. and dissected to obtain samples of blood and of infected and control muscle tissue. The tissue samples were weighed, and along with a standard amount of the injected dose, were counted using a gamma counter, and the percent injected dose (per gram of tissue) remaining in the tissues was determined. Ratios of percent of injected dose per gram of infected versus non-infected muscle tissue, and of infected muscle tissue versus blood, were calculated for each peptide. These results are presented in the following Table for the Tc-99m labeled reagent of the invention, having the formula formylMLFK(BAT).amide. (SEQ ID NO:17)

| Peptides | A | B | C | D | E |
|---|---|---|---|---|---|
| formylMLFK(BAT).amide SEQ ID NO: 19 | 0.0215 | 0.0028 | 7.68 | 0.006 | 3.58 |

A = % ID/gram infected muscle
B = % ID/gram control muscle
C = Ratio infected muscle:control muscle
D = Ratio infected muscle:blood

EXAMPLE 6

Localization and In Vivo Imaging of Somatostatin Receptor (SSTR)-Expressing Tumors in Rats In vivo imaging of somatostatin receptors expressed by rat tumor cells was performed essentially as described by Bakker et al. (1991, *Life Sciences* 49: 1593–1601).

CA20948 rat pancreatic tumor cells, thawed from frozen harvested tumor brei, were implanted intramuscularly in a suspension of 0.05 to 0.1 mL/animal, into the right hind thigh of 6 week old Lewis rats. The tumors were allowed to grow to approximately 0.5 to 2 g, harvested, and tumor brei was used to implant a second, naive set of Lewis rats. Passaging in this fashion was repeated to generate successive generations of tumor-bearing animals. The tumor-bearing animals used for the in vivo studies were usually from the third to fifth passage and carried 0.2 to 2 g tumors.

For studies of the specificity of radiotracer localization in the tumors, selected animals were given an subcutaneous SSTR-blocking dose (4 mg/kg) of octreotide 30 minutes prior to injection of the radiotracer. (This protocol has been shown by Bakker et al. to result in a lowering of $^{111}$In-[DTPA]octreotide tumor uptake by 40%.)

Third- to fifth-passage CA20948 tumor-bearing Lewis rats were restrained and injected intravenously via the dorsal tail vein with a dose of 0.15–0.20 mCi $^{99m}$Tc-labeled peptide corresponding to 3 to 8 μg peptide in 0.2 to 0.4 mL.

At selected times, the animals were sacrificed by cervical dislocation and selected necropsy was performed. Harvested tissue samples were weighed and counted along with an aliquot of the injected dose in a gamma well-counter.

The 90-minute biodistribution results of selected radiolabeled peptides are presented in Table I. Notably, $^{99m}$Tc-P587, $^{99m}$Tc-P617, $^{99m}$Tc-P726, and $^{99m}$Tc-P736 showed very high tumor uptake and tumor/blood ratios demonstrating their high specific uptake in target (tumor) tissue.

FIG. 1 shows an image of $^{99m}$Tc-P587 in a tumor-bearing rat. The high uptake in the tumor in the lower leg (arrow) is clearly visible.

$^{99m}$Tc-P587 uptake in tumors in rats was compared with and without pre-injection treatment with octreotide, a somatostatin analogue known to bind to the somatostatin receptor in vivo. In these experiments, receptor-blocking by administration of octreotide prior to administration of $^{99m}$Tc-P587 reduced specific tumor uptake of the radiolabeled peptide by 76%. These results confirmed that binding of $^{99m}$Tc-P587 in vivo was SSTR-specific.

TABLE III

| No. | Peptides | % ID/g | | |
|---|---|---|---|---|
| | | Tumor | Blood | Tumor/Blood |
| P736 | cyclo(N-methyl)FYW$_D$KV.Hcy.(CH$_2$CO.GGCRK.amide) | 2.1 | 0.24 | 9 |
| P587 | cyclo(N-methyl)FYW$_D$KV.Hcy.(CH$_2$CO.GGCK.amide) | 3.4 | 0.61 | 6 |
| P617 | cyclo(N-methyl)FYW$_D$KVKV.Hcy.(CH$_2$CO.GGCR.amide) | 6.7 | 0.73 | 9 |
| P726 | cyclo(N-methyl)FYW$_D$KVKV.Hcy.(CH$_2$CO.KKC.amide) | 2.5 | 0.30 | 8 |

What is claimed is:

1. A composition comprising:
   a) a peptide having specific binding properties and comprising from 3 to 100 amino acid residues, wherein one of said residues has a thiol sidechain; and
   b) a radiolabel complexing moiety,
   wherein:
   the moiety is covalently linked to said sidechain, and
   the specific binding properties of the peptide are retained.

2. The composition of claim 1 wherein the peptide and the moiety are covalently linked through a homocysteine residue.

3. A scintigraphic imaging agent comprising the composition of claim 1 and a radiolabel.

4. The agent of claim 3 wherein the radiolabel is technetium-99m, indium-111, or gallium-68.

5. A composition comprising:
   a) a peptide having specific binding properties and comprising from 3 to 100 amino acid residues, wherein said residue has a sidechain comprising amine or thiol; and
   b) a radiolabel complexing moiety having a formula selected from the group consisting of:

$$Cp(aa)Cp \qquad \qquad I.$$

wherein Cp is a protected cysteine and (aa) is any primary α- or β-amino acid not containing a thiol group;

III.

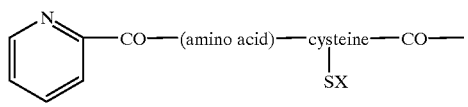

wherein
X=H or a protecting group;
(amino acid)=any primary α- or β-amino acid not containing a thiol group;

IV.

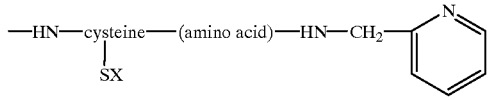

wherein
X=H or a protecting group;
(amino acid)=any primary α- or β-amino acid not containing a thiol group;

V.

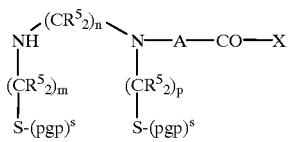

wherein
each $R^5$ is independently H, $CH_3$ or $C_2H_5$;
each $(pgp)^S$ is independently a thiol protecting group or H;
m, n and p are independently 2 or 3;
A=linear lower alkyl, cyclic lower alkyl, aryl, heterocyclyl, or a combination thereof;
X=peptide;
and

VI.

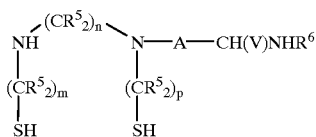

wherein
each $R^5$ is independently H, lower alkyl having 1 to 6 carbon atoms, phenyl, or phenyl substituted with lower alkyl or lower alkoxy;
m, n and p are independently 1 or 2;
A=linear lower alkyl, cyclic lower alkyl, aryl, heterocyclyl, or a combination thereof;
V=H or —CO-peptide;
$R^6$=H or peptide;
wherein when V=H, $R^6$=peptide and when $R^6$=H, V=—CO-peptide,
wherein:
the moiety is covalently linked to said sidechain; and
the specific binding properties of the peptide are retained.

6. The composition of claim 5 wherein the protected cysteine of formula I has a protecting group of a formula

wherein R is a lower alkyl group having 1 to 6 carbon atoms, 2-,3-,4-pyridyl, phenyl, or phenyl substituted with lower alkyl, hydroxy, lower alkoxy, carboxy, or lower alkoxycarbonyl.

7. The composition of claim 5, wherein the moiety has a formula:

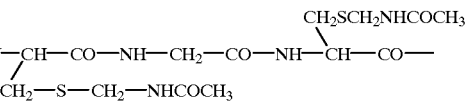

8. A scintigraphic imaging agent comprising the composition of claim 5 and a radiolabel.

9. The agent of claim 8 wherein the radiolabel is technetium-99m, indium-111, or gallium-68.

10. A composition comprising:
a) a peptide having specific binding properties and comprising from 3 to 100 amino acids; and
b) a radiolabel complexing moiety comprising a single thiol having a formula:

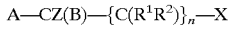   II.

wherein
A is H, HOOC, $H_2NOC$, (amino acid or peptide)-NHOC, (amino acid or peptide)-OOC, or $R^4$;
B is H, SH, —$NHR^3$, —$N(R^3)$-(amino acid or peptide), or $R^4$;
X is H, SH, —$NHR^3$, —$N(R^3)$-(amino acid or peptide), or $R^4$;
Z is a lower straight or branched chain or cyclic alkyl;
$R^1$, $R^2$, $R^3$, and $R^4$ are independently H or lower straight or branched chain or cyclic alkyl;
n is 0, 1, or 2;
(peptide) is a peptide of 2 to about 10 amino acids; and
where B is —$NHR^3$ or —$N(R^3)$-amino acid or peptide), X is SH, and n is 1 or 2;
where X is —$NHR^3$ or —$N(R^3)$-amino acid or peptide), B is SH, and n is 1 or 2;
where B is H or $R^4$, A is HOOC, $H_2NOC$, (amino acid or peptide)-NHOC, (amino acid or peptide)-OOC, X is SH, and n is 0 or 1;
where A is H or $R^4$, then where B is SH, X is —$NHR^3$ or —$N(R^3)$-amino acid or peptide) and where X is SH, B is —$NHR^3$ or —$N(R^3)$-(amino acid or peptide);
where X is H or $R^4$, A is HOOC, $H_2NOC$, (amino acid or peptide)-NHOC, (amino acid or peptide)-OOC, and B is SH;
where Z is methyl, X is methyl, A is HOOC, $H_2NOC$, (amino acid or peptide)-NHOC, (amino acid or peptide)-OOC, B is SH and n is 0;
and wherein the thiol is in the reduced form and (amino acid) is any primary α- or β-amino acid not containing a thiol group:
wherein:
the moiety is covalently linked to a sidechain of an amino acid of the peptide; and
the specific binding properties of the peptide are retained.

11. The composition of claim 10, wherein the moiety is selected from the group consisting of:

—(amino acid)¹—(amino acid)²—{A—CZ(B)—
    C(R¹R²)}ₙ—X};                                                    IIa.

—{A—CZ(B)—{C(R¹R²)}ₙ—X}—(amino acid)¹—
    (amino acid)²;                                                   IIb.

—(a primary α,ω- or β,ω-diamino acid)—(amino acid)—{A—
    CZ(B)—{C(R¹R²)}ₙ—X}—;                                            IIc.

and

—{A—CZ(B)—{C(R¹R²)}ₙ—X}—(amino acid)¹—(a primary
    α,ω- or β,ω-diamino acid);                                       IId.

wherein
  (amino acid)¹ and (amino acid)² are each independently
    any naturally-occurring, modified, substituted, or
    altered α- or β-amino acid not containing a thiol group.
12. A scintigraphic imaging agent comprising the composition of claim 10 and a radiolabel.
13. The agent of claim 12 wherein the radiolabel is technetium-99m, indium-111, or gallium-68.
14. A composition comprising:
  a) a peptide selected from the group consisting of:
    formyl-MLF
    (VGVAPG)₃amide
    (VPGVG)₄amide
    RALVDTLKFVTQAEGAKamide (SEQ ID NO.:1);
    RALVDTEFKVKQEAGAKamide (SEQ ID NO.:2);
    PLARITLPDFRLPEIAIPamide (SEQ ID NO.:3);
    GQQHHLGGAKAGDV (SEQ ID NO.:4);
    PLYKKIIKKLLES (SEQ ID NO.:5);
    LRALVDTLKamide (SEQ ID NO.:6);
    GGGLRALVDTLKamide (SEQ ID NO.:7);
    GGGLRALVDTLKFVTQAEGAKamide (SEQ ID NO.:8);
    GGGRALVDTLKALVDTLamide (SEQ ID NO.:9);
    GHRPLDKKREEAPSLRPAPPPISGGGYR (SEQ ID NO.:10);
    PSPSPIHPAHHKRDRRQamide (SEQ ID NO.:11);
    GGGF_D.Cpa.YW_DKTFTamide;

(SEQ ID NO.: 12)
    GGCNP.Apc.GDC
       \         /
        S - - - S (SYNRGDSTC)₃-TSEA
    GGGLRALVDTLKamide (SEQ ID NO.:13);
    GCGGGLRALVDTLKamide (SEQ ID NO.:14);
    GCYRALVDTLKFVTQAEGAKamide (SEQ ID NO.:15); and
    GC(VGVAPG)₃amide; and
  b) a radiolabel complexing moiety;
wherein:
  the moiety is covalently linked to a sidechain of an amino acid of the peptide; and
  the specific binding properties of the peptide are retained.
15. A composition comprising:
  a) a multiplicity of peptides having specific binding properties;
  b) a radiolabel complexing moiety covalently linked to a sidechain of an amino acid of each peptide; and
  c) a polyvalent linking moiety covalently linked to each peptide,
thereby forming a multimeric polyvalent reagent having a molecular weight less than about 20,000 daltons.

16. The composition of claim 15 wherein the polyvalent linking moiety is selected from the group consisting of bis-succinimidylmethylether, 4-(2,2-dimethylacetyl)benzoic acid, N-(2-(N',N'-bis(2-succinimido-ethyl)aminoethyl))-N⁶, N⁹-bis(2-methyl-2-mercaptopropyl)-6,9-diazanonanamide, tris(succinimidylethyl)amine, tris(acetamidoethyl)amine, bis(acetamidoethyl)ether, bis-(acetamidomethyl)ether, α,ε-bisacetyllysine, lysine and 1,8-bis-acetamido-3,6-dioxaoctane.

17. A complex formed by reacting the composition of claim 1 with technetium-99m in the presence of a reducing agent.

18. The complex of claim 17, wherein the reducing agent is selected from the group of a dithionite ion, a stannous ion, or a ferrous ion.

19. A complex formed by labeling the composition of claim 1 with technetium-99m by ligand exchange of a prereduced technetium-99m complex.

20. A kit for preparing a radiopharmaceutical preparation, said kit comprising a sealed vial containing a predetermined quantity of the composition of claim 1 and a sufficient amount of a reducing agent to label the reagent with technetium-99m.

21. A method of imaging a site within a mammalian body comprising the steps of administering an effective diagnostic amount of the agent of claim 4 and detecting the radiolabel localized at said site.

22. A process of preparing the composition of claim 1, wherein the peptide is chemically synthesized in vitro.

23. The process of claim 22, wherein the peptide is synthesized by solid phase peptide synthesis.

24. The composition of claim 1 wherein the peptide and the moiety comprise a cyclic peptide.

25. The composition of claim 5 wherein the moiety has formula:

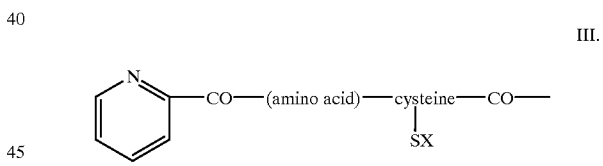

III.

wherein
  X=H or a protecting group; and
  (amino acid)=any primary α- or β-amino acid not containing a thiol group.

26. The composition of claim 5 wherein the moiety has formula:

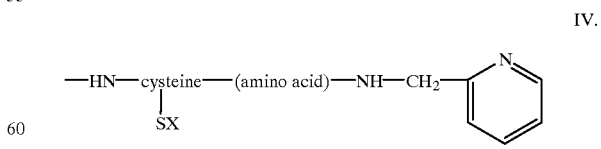

IV.

wherein
  X=H or a protecting group; and
  (amino acid)=any primary α- or β- amino acid not containing a thiol group.

27. The composition of claim 5 wherein the moiety has formula:

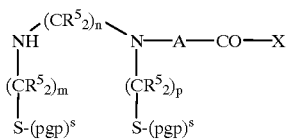

wherein each $R^5$ is independently H, $CH_3$ or $C_2H_5$;

each $(pgp)^S$ is independently a thiol protecting group or H;

m, n and p are independently 2 or 3;

A=linear lower alkyl, cyclic lower alkyl, aryl, heterocyclyl, or a combination thereof;

X=peptide.

28. The composition of claim 5 wherein the moiety has formula:

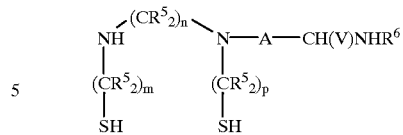

wherein each $R^5$ is independently H, lower alkyl having 1 to 6 carbon atoms, phenyl, or phenyl substituted with lower alkyl or lower alkoxy;

m, n and p are independently 1 or 2;

A=linear lower alkyl, cyclic lower alkyl, aryl, heterocyclyl, or a combination thereof;

V=H or —CO-peptide;

$R^6$=H or peptide;

and wherein when V=H, $R^6$=peptide and when $R^6$=H, V=—CO-peptide.

29. The composition of claim 14 wherein the peptide has the amino acid sequence PLYKKIKKLLES.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 17
        (D) OTHER INFORMATION: /product= "lysine 17 is amidated"
            /label= amide (xi) SEQUENCE DESCRIPTION: SEQ ID NO:1:

Arg Ala Leu Val Asp Thr Leu Lys Phe Val Thr Gln Ala Glu Gly Ala
1               5                   10                  15

Lys (2) INFORMATION FOR SEQ ID NO:2:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 17
        (D) OTHER INFORMATION: /product= "lysine 17 is amidated"
            /label= amide (xi) SEQUENCE DESCRIPTION: SEQ ID NO:2:

Arg Ala Leu Val Asp Thr Glu Phe Lys Val Lys Gln Glu Ala Gly Ala
1               5                   10                  15

Lys (2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: Not Relevant (D) TOPOLOGY: linear (ii) MOLECULE TYPE: peptide (ix) FEATURE:
    (A) NAME/KEY: Modified-site
    (B) LOCATION: 18
    (D) OTHER INFORMATION: /product= "proline 18 is amidated"
        /label= amide (xi) SEQUENCE DESCRIPTION: SEQ ID NO:3:

```
Pro Leu Ala Arg Ile Thr Leu Pro Asp Phe Arg Leu Pro Glu Ile Ala
1               5                   10                  15

Ile Pro
```

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Gly Gln Gln His His Leu Gly Gly Ala Lys Ala Gly Asp Val
1               5                   10
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Pro Leu Tyr Lys Lys Ile Ile Lys Lys Leu Leu Glu Ser
1               5                   10
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /product= "lysine 9 is amidated"
            /label= amide (xi) SEQUENCE DESCRIPTION: SEQ ID NO:6:

```
Leu Arg Ala Leu Val Asp Thr Leu Lys
1               5
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (ix) FEATURE:
            (A) NAME/KEY: Modified-site
            (B) LOCATION: 12
            (D) OTHER INFORMATION: /product= "lysine 12 is amidated"
                /label= amide (xi) SEQUENCE DESCRIPTION: SEQ ID NO:7:

Gly Gly Gly Leu Arg Ala Leu Val Asp Thr Leu Lys
1               5                  10

(2) INFORMATION FOR SEQ ID NO:8:

(i) SEQUENCE CHARACTERISTICS:
            (A) LENGTH: 21 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 21
            (D) OTHER INFORMATION: /product= "lysine 21 is amidated"
                /label= amide (xi) SEQUENCE DESCRIPTION: SEQ ID NO:8:

Gly Gly Gly Leu Arg Ala Leu Val Asp Thr Leu Lys Phe Val Thr Gln
1               5                  10                  15

Ala Glu Gly Ala Lys
            20

(2) INFORMATION FOR SEQ ID NO:9:

(i) SEQUENCE CHARACTERISTICS:
            (A) LENGTH: 17 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 17
            (D) OTHER INFORMATION: /product= "leucine 17 is amidated"
                /label= amide (xi) SEQUENCE DESCRIPTION: SEQ ID NO:9:

Gly Gly Gly Arg Ala Leu Val Asp Thr Leu Lys Ala Leu Val Asp Thr
1               5                  10                  15

Leu (2) INFORMATION FOR SEQ ID NO:10:

(i) SEQUENCE CHARACTERISTICS:
            (A) LENGTH: 28 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:10:

Gly His Arg Pro Leu Asp Lys Lys Arg Glu Glu Ala Pro Ser Leu Arg
1               5                  10                  15

Pro Ala Pro Pro Pro Ile Ser Gly Gly Gly Tyr Arg
            20                  25

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 17
        (D) OTHER INFORMATION: /product= "glutamine 17 is
            amidated"
            /label= amide (xi) SEQUENCE DESCRIPTION: SEQ ID NO:11:

Pro Ser Pro Ser Pro Ile His Pro Ala His His Lys Arg Asp Arg Arg
1            5                10              15

Gln (2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: circular (ii) MOLECULE TYPE: peptide (ix) FEATURE:
        (A) NAME/KEY: Disulfide-bond
        (B) LOCATION: 3..9

(ix) FEATURE:
        (A) NAME/KEY: Modified-site
        (B) LOCATION: 6
        (D) OTHER INFORMATION: /product= "residue 6 is
            L-[S-(3-aminopropyl)cysteine]"

(xi) SEQUENCE DESCRIPTION: SEQ ID NO:12:

Gly Gly Cys Asn Pro Xaa Gly Asp Cys
1            5

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /product= "lysine 12 is amidated"
            /label= amide (xi) SEQUENCE DESCRIPTION: SEQ ID NO:13:

Gly Gly Gly Leu Arg Ala Leu Val Asp Thr Leu Lys
1            5                10

(2) INFORMATION FOR SEQ ID NO:14:

(i) SEQUENCE CHARACTERISTICS:
        (A) LENGTH: 14 amino acids
        (B) TYPE: amino acid

```
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 14
            (D) OTHER INFORMATION: /product= "lysine 14 is amidated"
                /label= amide (xi) SEQUENCE DESCRIPTION: SEQ ID NO:14:

Gly Cys Gly Gly Gly Leu Arg Ala Leu Val Asp Thr Leu Lys
1               5                   10

(2) INFORMATION FOR SEQ ID NO:15:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 20
            (D) OTHER INFORMATION: /product= "lysine 20 is amidated"
                /label= amide (xi) SEQUENCE DESCRIPTION: SEQ ID NO:15:

Gly Cys Tyr Arg Ala Leu Val Asp Thr Leu Lys Phe Val Thr Gln Ala
1               5                   10                  15

Glu Gly Ala Lys
            20

(2) INFORMATION FOR SEQ ID NO:16:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "glycine 1 contains a
                chloroacetyl group"
                /label= ClCH2CO (ix) FEATURE:
            (A) NAME/KEY: Modified-site
            (B) LOCATION: 4
            (D) OTHER INFORMATION: /product= "lysine 4 is amidated"
                /label= amide (xi) SEQUENCE DESCRIPTION: SEQ ID NO:16:

Gly Gly Cys Lys
1

(2) INFORMATION FOR SEQ ID NO:17:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: linear (ii) MOLECULE TYPE: peptide
```

(ix) FEATURE:
            (A) NAME/KEY: Modified-site
            (B) LOCATION: 1
            (D) OTHER INFORMATION: /product= "methionine 1 is
                formylated"
                /label= formyl (ix) FEATURE:
            (A) NAME/KEY: Modified-site
            (B) LOCATION: 4
            (D) OTHER INFORMATION: /product= "lysine 4 is linked to a
                (BAT) chelator"
                /label= BAT (xi) SEQUENCE DESCRIPTION: SEQ ID NO:17:

Met Leu Phe Lys
1

(2) INFORMATION FOR SEQ ID NO:18:

(i) SEQUENCE CHARACTERISTICS:
            (A) LENGTH: 9 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "methionine 1 is
                formylated"
                /label= formyl (ix) FEATURE:
            (A) NAME/KEY: Modified-site
            (B) LOCATION: 4
            (D) OTHER INFORMATION: /product= "lysine 4 is linked to
                BAT chelator"
                /label= BAT (ix) FEATURE:
            (A) NAME/KEY: Modified-site
            (B) LOCATION: 9
            (D) OTHER INFORMATION: /product= "lysine 9 is amidated"
                /label= amide (xi) SEQUENCE DESCRIPTION: SEQ ID NO:18:

Met Leu Phe Lys Lys Lys Lys Lys Lys
1               5

(2) INFORMATION FOR SEQ ID NO:19:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "methionine 1 is
                formylated"
                /label= formyl (ix) FEATURE:
            (A) NAME/KEY: Modified-site
            (B) LOCATION: 4
            (D) OTHER INFORMATION: /product= "lysine 4 is linked to a
                BAT chelator"
                /label= BAT (ix) FEATURE:
              (A) NAME/KEY: Modified-site
              (B) LOCATION: 10
              (D) OTHER INFORMATION: /product= "serine 10 is amidated"
                  /label= amide (xi) SEQUENCE DESCRIPTION: SEQ ID NO:19:

Met Leu Phe Lys Gly Ser Gly Ser Gly Ser
1               5                   10

(2) INFORMATION FOR SEQ ID NO:20:

(i) SEQUENCE CHARACTERISTICS:
              (A) LENGTH: 5 amino acids
              (B) TYPE: amino acid
              (C) STRANDEDNESS: Not Relevant
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "methionine 1 is
                  formylated"
                  /label= formyl (ix) FEATURE:
              (A) NAME/KEY: Modified-site
              (B) LOCATION: 4
              (D) OTHER INFORMATION: /product= "lysine 4 is linked to a
                  BAT chelator"
                  /label= BAT (xi) SEQUENCE DESCRIPTION: SEQ ID NO:20:

Met Leu Phe Lys Glu
1               5

(2) INFORMATION FOR SEQ ID NO:21:

(i) SEQUENCE CHARACTERISTICS:
              (A) LENGTH: 7 amino acids
              (B) TYPE: amino acid
              (C) STRANDEDNESS: Not Relevant
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "methionine 1 is
                  formylated"
                  /label= formyl (ix) FEATURE:
              (A) NAME/KEY: Modified-site
              (B) LOCATION: 4
              (D) OTHER INFORMATION: /product= "lysine 4 is linked to a
                  BAT chelator"
                  /label= BAT (xi) SEQUENCE DESCRIPTION: SEQ ID NO:21:

Met Leu Phe Lys Glu Gly Glu
1               5

(2) INFORMATION FOR SEQ ID NO:22:

(i) SEQUENCE CHARACTERISTICS:
              (A) LENGTH: 18 amino acids
              (B) TYPE: amino acid
              (C) STRANDEDNESS: Not Relevant
              (D) TOPOLOGY: linear

```
        (ii) MOLECULE TYPE: peptide (ix) FEATURE:
             (A) NAME/KEY: Modified-site
             (B) LOCATION: 18
             (D) OTHER INFORMATION: /product= "lysine 18 is linked to a
                 BAT chelator"
                 /label= BAT (ix) FEATURE:
             (A) NAME/KEY: Modified-site
             (B) LOCATION: 18
             (D) OTHER INFORMATION: /product= "lysine 18 is amidated"
                 /label= amide (xi) SEQUENCE DESCRIPTION: SEQ ID NO:22:

Tyr Arg Ala Leu Val Asp Thr Leu Lys Phe Val Thr Gln Ala Glu Gly
1               5                   10                  15

Ala Lys (2) INFORMATION FOR SEQ ID NO:23:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "X is pyroglutamic acid"

(ix) FEATURE:
             (A) NAME/KEY: Modified-site
             (B) LOCATION: 15
             (D) OTHER INFORMATION: /product= "lysine 15 is linked to a
                 BAT chelator"
                 /label= BAT (ix) FEATURE:
             (A) NAME/KEY: Modified-site
             (B) LOCATION: 15
             (D) OTHER INFORMATION: /product= "lysine 15 is amidated"
                 /label= amide (xi) SEQUENCE DESCRIPTION: SEQ ID NO:23:

Xaa Gly Val Asn Asp Asn Glu Glu Gly Phe Phe Ser Ala Arg Lys
1               5                   10                  15
```